United States Patent
Schmid et al.

(10) Patent No.: US 6,569,410 B1
(45) Date of Patent: May 27, 2003

(54) SUN PROTECTION COMPOSITIONS CONTAINING UV PROTECTION FACTORS AND ESTERS OF HYDROXYCARBOXYLIC ACIDS AND ALK(EN)YL OLIGOGLYCOSIDES

(75) Inventors: Karl Heinz Schmid, Mettmann (DE); Bernd Fabry, Korschenbroich (DE); Josef Koester, Duesseldorf (DE); Hermann Hensen, Haan (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/958,700

(22) PCT Filed: Apr. 5, 2000

(86) PCT No.: PCT/EP00/03016

§ 371 (c)(1),
(2), (4) Date: Jan. 28, 2002

(87) PCT Pub. No.: WO00/61078

PCT Pub. Date: Oct. 19, 2000

(30) Foreign Application Priority Data

Apr. 10, 1999 (DE) .......................... 199 16 208

(51) Int. Cl.$^7$ .................. A61K 7/42; A61K 7/44; A61K 7/00
(52) U.S. Cl. .................. 424/59; 424/60; 424/400; 424/401
(58) Field of Search .................. 424/59, 60, 400, 424/401

(56) References Cited

U.S. PATENT DOCUMENTS

| | | |
|---|---|---|
| 4,172,887 A | 10/1979 | Vanlerberghe et al. |
| 4,797,481 A | 1/1989 | Garlisi et al. |
| 5,508,394 A | 4/1996 | Kappes et al. |
| 5,705,169 A | 1/1998 | Stein et al. |
| 5,730,960 A | 3/1998 | Stein et al. |
| 5,756,110 A | 5/1998 | Allard et al. |
| 6,193,960 B1 | 2/2001 | Metzger et al. |

FOREIGN PATENT DOCUMENTS

| | | |
|---|---|---|
| DE | 1 165 574 | 3/1964 |
| DE | 20 24 051 C3 | 10/1979 |
| DE | 41 08 626 A1 | 9/1992 |
| DE | 41 42 131 A1 | 6/1993 |
| DE | 196 15 035 A1 | 10/1997 |
| EP | 0 258 814 A2 | 3/1988 |
| EP | 0 261 812 A1 | 3/1988 |
| EP | 0 514 067 A1 | 11/1992 |
| EP | 0 667 144 A1 | 8/1995 |
| EP | 0 693 471 B1 | 1/1998 |
| EP | 0 694 521 B1 | 1/1998 |
| EP | 0 818 450 A1 | 1/1998 |
| FR | 2 252 840 | 8/1975 |
| GB | 962919 | 7/1964 |
| GB | 1 333 475 | 10/1973 |
| WO | 97/03643 | 2/1997 |

OTHER PUBLICATIONS

Finkel, "Formuierung kosmetischer Sonnenschultzmittel", SÖFW–Journal, vol. 122, (1996), pp. 543–546 & 548.

Todd, et al., "Volatile silicone fluids for cosmetic formulations", Cosmetics and Toiletries, vol. 91, (Jan., 1976), pp. 29–32.

Tronnier, et al., "Experimentelle Untersuchungen zur Wirkungsweise aluminiumhaltiger Antiperspiranzien", J. Soc. Cosmetic Chemists, vol. 24, (1973), pp. 281–290.

Graham, et al., "Inhibition of the mitochondrial oxidation of octanoate by salicylic acid and related compounds", J. Pharm. Pharmac., vol. 26, (1974), pp. 531–534.

Lochhead, et al., "Encyclopedia of Polymers and Thickeners for Cosmetics", Cosmetics & Toiletries, vol. 108, (May, 1993), pp. 95–114, 116–124, 127–130, 133–135.

"Kosmetische Färbemittel", Farbstoffcommission der Deutschen Forschungsgemeinschaft, Verlag Chemie, Weinheim, (1984), pp. 81–106.

*Primary Examiner*—Shelley A. Dodson
(74) *Attorney, Agent, or Firm*—Aaron R. Ettelman

(57) ABSTRACT

Cosmetic preparations which contain (a) an ester of a hydroxycarboxylic acid and an alk(en)yl oligoglycoside, and (b) a UV protection factor; are described. The correspond to the general formula (I):

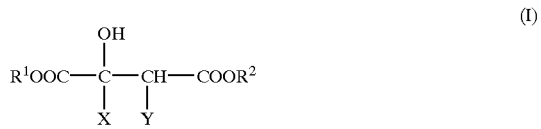

wherein X represents a hydrogen or a —$CH_2COOR^3$ substituent, Y represents a hydrogen or a hydroxyl substituent, $R^1$, $R^2$, and $R^3$ each independently represents a substituent selected from the group consisting of hydrogen, alkali metals, alkaline earth metals, ammonium, alkyl ammoniums, hydroxyalkyl ammoniums, glucammonium, and residues of alk(en)yl oligoglycosides; wherein at least one of $R^1$, $R^2$ and $R^3$ represents a residue of an alk(en)yl oligoglycosides, and with the proviso that, where X represents a —$CH_2COOR^3$ group, Y is hydrogen.

20 Claims, No Drawings

SUN PROTECTION COMPOSITIONS CONTAINING UV PROTECTION FACTORS AND ESTERS OF HYDROXYCARBOXYLIC ACIDS AND ALK(EN)YL OLIGOGLYCOSIDES

BACKGROUND OF THE INVENTION

Under the influence of solar radiation, the pigmenting of normal skin leads to the formation of melanins. Exposure to long-wave UV-A light results in darkening of the melanins present in the epidermis without any harmful effects while exposure to short-wave UV-B radiation results in the formation of new melanin. However, before the protective pigment can be formed, the skin is exposed to the effect of unfiltered radiation which can lead to reddening of the skin (erythema), inflammation of the skin (sunburn) or even to blisters, depending on the exposure time. The strain on the organism associated with such skin lesions, for example in connection with the distribution of histamines, can additionally lead to headache, lassitude, fever, heart and circulation problems and the like. The consumer seeking to protect himself/herself against the harmful effects of the sun can choose from a range of products which, for the most part, are oils and milky emulsions which, besides a few skin-care ingredients, contain above all UV filters.

Nevertheless, there is a continuing need on the market for products with an improved performance spectrum. Of particular interest in this regard are preparations which enable relatively large amounts of UV filters to be incorporated without any phase separation or sedimentation occurring during storage. Where relatively large quantities of titanium dioxide are incorporated, a formulation produced by the phase inversion temperature method, as described for example in European patent application EP 0 667 144 A1 (L'Oreal), tends to separate the dispersed solid very quickly. Another problem is that many UV filters are capable of interacting with the other ingredients of the formulation, resulting in a chemical reaction and also in a reduction in storage stability. Finally, consumers prefer transparent formulations which show high dermatological compatibility, even when applied to very sensitive skin.

Accordingly, the complex problem addressed by the present invention was to provide sun protection compositions which would be distinguished by particular phase stability, stability in storage on exposure to heat and compatibility with sensitive skin.

BRIEF SUMMARY OF THE INVENTION

The present invention relates, in general, to cosmetics and more particularly to sun protection compositions containing special esters of hydroxycarboxylic acids together with UV protection filters or pigments and to the use of the mixtures in sun protection compositions.

It has surprisingly been found that the special hydroxycarboxylic acid esters are capable of both stably emulsifying liquid UV protection factors and reliably dispersing even relatively large quantities of crystalline filters or pigments, even on exposure to heat. The invention includes the observation that the hydroxycarboxylic acid esters also considerably improve the photostability of a large number of UV protection filters.

DETAILED DESCRIPTION OF THE INVENTION

Esters of hydroxycarboxylic acids and alkyl and alkenyl oligoglycosides are known nonionic surfactants which correspond to formula (I):

where X is hydrogen or a $CH_2COOR^3$ group, Y is hydrogen or a hydroxyl group, $R^1$, $R^2$ and $R^3$ independently of one another represent hydrogen, an alkali metal or alkaline earth metal, ammonium, alkyl ammonium, hydroxyalkyl ammonium, glucammonium or the residue of an alkyl and/or alkenyl oligoglycoside corresponding to formula (II):

in which $R^4$ is an alkyl and/or alkenyl group containing 4 to 22 carbon atoms, G is a sugar unit containing 5 or 6 carbon atoms and p is a number of 1 to 10, with the provisos that, where X is a $CH_2COOR^3$ group, Y is hydrogen and at least one of the substituents $R^1$, $R^2$ and $R^3$ is a glycoside unit. The production and use of these compounds as high-foaming surfactants in cosmetic preparations is known from European patent EP 0 258 814 B1 (Auschem) to which reference is made here.

The acid component of the nonionic surfactants may be derived from malic acid, tartaric acid or citric acid and mixtures thereof. Depending on the number of hydroxyl groups present in the acid component, mono-, di- or triesters and technical mixtures thereof may be used. However, monoesters or high-monomer mixtures, which may be obtained by the expert in accordance with the teaching of the above-cited EP 0 258 814 B1, are preferably used.

The alkyl and/or alkenyl oligoglycoside component may be derived from aldoses or ketoses containing 5 or 6 carbon atoms, preferably glucose. Accordingly, the preferred nonionic surfactants are esters of alkyl and/or alkenyl oligoglucosides. The index p in general formula (II) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Esters of which the alkyl and/or alkenyl oligoglycoside component has an average degree of oligomerization p of 1.1 to 3.0 are preferably used. Alkyl and/or alkenyl oligoglycoside esters having a degree of oligomerization of less than 1.7 and, more particularly, between 1.2 and 1.4 are preferred from the applicational point of view. The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. $C_{9-11}$ or $C_{8-10}$ alkyl oligoglucoside esters with a DP of 1 to 3, of which the alkyl group is derived from corresponding oxoalcohols or alcohols which are obtained as first runnings in the separation of technical $C_{8-18}$ coconut oil fatty alcohol by distillation and which may contain less than 6% by weight of $C_{12}$ alcohol as an impurity, are preferred. In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucoside esters based on hydrogenated $C_{12/14}$ coconut oil fatty alcohol having a DP of 1 to 3 are preferred. Such products are commercially obtainable as Eucarol®.

The invention includes the observation that mixtures of hydroxycarboxylic acid alkyl and/or alkenyl glycoside esters and alkyl and/or alkenyl oligoglycosides together with UV protection factors give particularly stable emulsions. In the most simple cases, these ternary mixtures may be prepared by mixing the three components. In one particular embodiment of the invention, however, UV protection factors or UV protection pigments are used together with hydroxycarboxylic acid glycoside esters which still contain 1 to 50, preferably 5 to 25 and more particularly 10 to 15% by weight of unesterified glycosides. Normally, the preparations may contain the hydroxycarboxylic acid esters in total quantities of 0.1 to 15, preferably 0.5 to 10 and more particularly 1 to 5% by weight.

UV Protection Factors

UV protection factors are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor, as described in EP 0693471 B1;

4-aminobenzoic acid derivatives, preferably 4-(dimethylamino)-benzoic acid-2-ethylhexyl ester, 4-(dimethylamino)benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone, as described in EP0 818450A1;

propane-1,3-diones such as, for example, 1-(4-tert.butylphenyl)-3-(4'-methoxyphenyl)propane-1,3-dione;

ketotricyclo(5.2.1)decane derivatives, as described in EP 0 694 521 B1.

Suitable Water-soluble Substances are 2-phenylbenzimidazole-5-sulfonic acid and alkali metal, alkaline earth metal, ammonium, alkylammonium, alkanolammonium and glucam-monium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example 1-(4'-tert.butylphenyl)-3-(4'-methoxyphenylypropane-1,3-dione, 4-tert-butyl4'-methoxydibenzoylmethane (Parsol 1789) or 1-phenyl-3-(4'-isopropylphenyl)-propane-1,3-dione. The UV-A and UV-B filters may of course also be used in the form of mixtures. Besides the soluble substances mentioned, insoluble UV protection pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have an average diameter of less than 100 nm, preferably from 5 to 50 nm and more preferably from 15 to 30 nm. They may be spherical in shape although ellipsoidal particles or other non-spherical particles may also be used. The pigments may also be surface-treated, i.e. hydrophilicized or hydrophobicized. Typical examples are coated titanium dioxides such as, for example, Ttitandioxid T 805 (Degussa) or Eusolex® T2000 (Merck). Suitable hydrophobic coating materials are, above all, silicones and especially trialkoxyoctyl silanes or simethicones. So-called micro- or nanopigments are preferably used in sun protection products. Micronized zinc oxide is preferably used. Other suitable UV filters can be found in P. Finkel's review in SÖFW-Journal 122, 543(1996).

Besides the two above-mentioned groups of primary protection factors, secondary protection factors of the antioxidant type may also be used. Secondary sun protection factors of the antioxidant type interrupt the photochemical reaction chain which is initiated when UV rays penetrate into the skin. Typical examples of suitable antioxidants are amino acids (for example glycine, histidine, tyrosine, tryptophane) and derivatives thereof, imidazoles (for example urocanic acid) and derivatives thereof, peptides, such as D,L-carnosine, D-camosine, L-camosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycbosyl rutin, ferulic acid, furfurylidene glucitol, camosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for he purposes of the invention (salts, esters, ethers, sugars, nucleotides, nucleosides, peptides and lipids).

Normally, the preparations may contain the UV protection factors in total quantities of 0.1 to 25, preferably 0.5 to 10 and more particularly 1 to 5% by weight.

Commercial Applications

The special hydroxycarboxylic acid esters have been found to be excellent emulsifiers for liquid UV protection factors and are capable of reliably dispersing crystalline filters or pigments, even on exposure to heat. Accordingly, the present invention also relates to their use as emulsifiers or dispersants for the production of sun protection compositions in which they may be present in quantities of 0.1 to 15, preferably 0.5 to 10 and more particularly 1 to 50% by weight, based on the composition.

Cosmetic and/or Pharmaceutical Preparations

The mixtures according to the invention may be used for the production of cosmetic. preparations, for example hair shampoos, hair lotions, foam baths, shower baths, creams, gels, lotions, alcoholic and aqueous/alcoholic solutions, emulsions, wax/fat compounds, stick preparations, powders or ointments. These preparations may also contain mild surfactants, oil components, emulsifiers, superfatting agents, pearlizing waxes, consistency factors, thickeners, polymers, silicone compounds, fats, waxes, stabilizers, biogenic agents, deodorizers, antidandruff agents, film formers, swelling agents, hydrotropes, preservatives, insect repellents, self-tanning agents, solubilizers, perfume oils, dyes, germ inhibitors and the like as further auxiliaries and additives.

Typical examples of suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein fatty acid condensates, preferably based on wheat proteins.

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl nyristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of hydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons, for example squalane, squalene or dialkyl cyclohexanes.

Suitable emulsifiers are, for example, nonionic surfactants from at least one of the following groups:
(1) products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and to alkylphenols containing 8 to 15 carbon atoms in the alkyl group;
(2) $C_{2/18}$ fatty acid monoesters and diesters of products of the addition of 1 to 30 moles of ethylene oxide onto glycerol;
(3) glycerol monoesters and diesters and sorbitan monoesters and diesters of saturated and unsaturated fatty acids containing 6 to 22 carbon atoms and ethylene oxide adducts thereof;
(4) alkyl mono- and oligoglycosides containing 8 to 22 carbon atoms in the alkyl group and ethoxylated analogs thereof;
(5) adducts of 15 to 60 moles of ethylene oxide with castor oil and/or hydrogenated castor oil;
(6) polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;
(7) products of the addition of 2 to 15 moles of ethylene oxide onto castor oil and/or hydrogenated castor oil;
(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);
(9) mono-, di and trialkyl phosphates and mono-, di- and/or tri-PEG-alkyl phosphates and salts thereof;
(10) wool wax alcohols;
(11) polysiloxane/polyalkyl polyether copolymers and corresponding derivatives;
(12) mixed esters of pentaerythritol, fatty acids, citric acid and fatty alcohol according to DE 1165574 PS and/or mixed esters of fatty acids containing 6 to 22 carbon atoms, methyl glucose and polyols, preferably glycerol or polyglycerol,
(13) polyalkylene glycols and
(14) glycerol carbonate.

The addition products of ethylene oxide and/or propylene oxide with fatty alcohols, fatty acids, alkylphenols, glycerol mono- and diesters and sorbitan mono- and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{2/18}$ fatty acid monoesters and diesters of adducts of ethylene oxide with glycerol are known as refatting agents for cosmetic formulations from DE 2024051 PS.

$C_{8/18}$ alkyl mono- and oligoglycosides, their production and their use as surfactants are known from the prior art. They are produced in particular by reaction of glucose or oligosaccharides with primary alcohols containing 8 to 18 C atoms. So far as the glycoside component is concerned, both monoglycosides, in which a cyclic sugar unit is attached to the fatty alcohol by a glycoside linkage, and oligomeric glycosides with a degree of oligomerization of preferably up to about 8 are suitable. The degree of oligomerization is a statistical mean value on which a homolog distribution typical of such technical products is based.

Zwitterionic surfactants may also be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known by the CTFA name of Cocamidopropyl Betaine is particularly preferred. Other suitable emulsifiers are ampholytic surfactants. Ampholytic surfactants are surface-active compounds which, in addition to a $C_{8/18}$ alkyl or acyl group, contain at least one free amino group and at least one —COOH or —$SO_3H$ group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides the amphoteric or zwitterionic emulsifiers, cationic emulsifiers, preferably of the esterquat type, may also be used.

The superfatting agents used may be such substances as, for example, lanolin and lecithin and polyethoxylated or acylated lanolin and lecithin derivatives, polyol fatty acid esters, monoglycerides and fatty acid alkanolamides, the latter also serving as foam stabilizers.

Suitable pearlizing waxes are, for example, alkylene glycol esters, particularly ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, for example fatty alcohols, fatty ketones, fatty aldehydes, fatty ethers and fatty carbonates which contain a total of at least 24 carbon atoms, especially laurone and distearyl ether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups; and mixtures thereof.

Suitable consistency factors are, above all, fatty alcohols or hydroxyfatty alcohols containing 12 to 22 and preferably 16 to 18 carbon atoms and, in addition, partial glycerides, fatty acids or hydroxyfatty acids. These substances are preferably used in combination with alkyl oligoglucosides and/or fatty acid-N-methyl glucamides of the same chain length and/or polyglycerol poly-12-hydroxystearates. Suitable thickeners are, for example, Aerosil types (hydrophilic silicas), polysaccharides, more particularly xanthan gum, guar guar, agar agar, alginates and tyloses, carboxymethyl cellulose and hydroxyethyl cellulose, relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols such as, for example, pentaerythritol or trimethylol propane, narrow-range fatty alcohol ethoxylates or alkyl oligoglucosides and electrolytes such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, Amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2 252 840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolyrmers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Typical examples of fats are glycerides while suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes, microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Suitable deodorizers are, for example, antiperspirants, such as aluminium chlorhydrates. These antiperspirants are colorless hygroscopic crystals which readily deliquesce in air and which accumulate when aqueous aluminium chloride solutions are concentrated by evaporation. Aluminium chlorhydrate is used for the production of perspiration-inhibiting and deodorizing compositions and probably acts by partially blocking the sweat glands through the precipitation of proteins and/or polysaccharides [cf. J. Soc. Cosm. Chem. 24, 281 (1973)]. For example, an aluminium chlorhydrate which corresponds to the formula $[Al_2(OH)_5Cl].2.5H_2O$ and which is particularly preferred for the purposes of the invention is commercially available under the name of Locron® from Hoechst AG of Frankfurt, FRG [cf. J. Pharm. Pharmcol. 26, 531 (1975)]. Besides the chlorhydrates, aluminium hydroxylactates and acidic aluminium/zirconium salts may also be used. Other suitable deodorizers are esterase inhibitors, preferably trialkyl citrates, such as trimethyl citrate, tripropyl citrate, triisopropyl citrate, tributyl citrate and, in particular, triethyl citrate (Hydagen® CAT, Henkel KGaA, Düsseldorf, FRG). Esterase inhibitors inhibit enzyme activity and thus reduce odor formation. The free acid is probably released through the cleavage of the citric acid ester, reducing the pH value of the skin to such an extent that the enzymes are inhibited. Other esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester. Antibacterial agents which influence the germ flora and destroy or inhibit the growth of perspiration-decomposing bacteria, may also be present in stick products. Examples of such antibacterial agents are chitosan, phenoxyethanol and chlorhexidine gluconate. 5-Chloro-2-(2,4-dichlorophenoxy)-phenol, which is marketed under the name of Irgasan® by Ciba-Geigy of Basel, Switzerland, has also proved to be particularly effective.

Suitable antidandruff agents are climbazol, octopirox and zinc pyrithione. Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Suitable swelling agents for aqueous phases are montmorillonites, clay minerals, Pemulen and alkyl-modified Carbopol types (Goodrich). Other suitable polymters and swelling agents can be found in R. Lochhead's review in Cosm. Toil. 108, 95 (1993).

In addition, hydrotropes such as, for example, ethanol, isopropyl alcohol or polyols may be used to improve flow behavior. Suitable polyols preferably contain 2 to 15 carbon atoms and at least two hydroxyl groups. The polyols may contain Other functional groups, especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols having an average molecular weight of 100 to 1,000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms such as, for example, sorbitol or mannitol;

sugars containing 5 to 12 carbon atoms such as, for example, glucose or sucrose;

aminosugars such as, for example, glucamine;

dialcoholamines, such as diethanolamine or 2-aminopropane-1,3-diol.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Insect Repellent 3535. A suitable self-tanning agent is dihydroxyacetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geraniol oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106. These dyes are normally used in concentrations of 0.001 to 0.1% by weight, based on the mixture as a whole.

Typical examples of germ inhibitors are preservatives which act specifically against gram-positive bacteria such as, for example, 2,4,4'-trichloro-2'-hydroxydiphenyl ether, chlorhexidine (1,6-di-(4-chlorophenylbiguanido)-hexane) or TCC (3,4,4'-trichlorocarbanilide). Numerous perfumes and essential oils also have antimicrobial properties. Typical examples are the active substances eugenol, menthol and thymol in clove, mint and thyme oil. An interesting natural deodorant is the terpene alcohol farnesol (3,7,11-trimethyl-2,6,10-dodecatrien-1-ol) which is present in linden blossom oil and which smells of lily-of-the-valley. Glycerol monolaurate has also been successfully used as a bacteriostatic agent. The percentage content of the additional germ-inhibiting agents is normally about 0.1 to 2% by weight, based on the solids component of the preparations.

The total percentage content of auxiliaries and additives may be from 1 to 50% by weight and is preferably from 5 to 40% by weight, based on the particular composition. The preparations may be produced by standard hot or cold processes and are preferably produced by the phase inversion temperature method.

EXAMPLE

In order to investigate stability in storage, preparations of various UV protection factors/pigments and emulsifiers or dispersants were stored for 1 to 4 weeks at 20 and 40° C. (++) means stable, no sedimentation/phase separation, (+) means small signs of sedimentation/phase separation and (−) means unstable. The results are set out in Table 1. Examples 1 to 6 correspond to the invention, Examples C1 and C2 are intended for comparison. All quantities are percentages by weight.

TABLE 1

Emulsions/dispersions of UV protection filters and pigments

|  | 1 | 2 | 3 | 4 | 5 | 6 | C1 | C2 |
|---|---|---|---|---|---|---|---|---|
| Composition |  |  |  |  |  |  |  |  |
| Sodium Laurylglucoside Citrate | 3.0 | — | — | 2.0 | — | — | — | — |
| Sodium Laurylglucoside Malate | — | 3.0 | — | — | 2.0 | — | — | — |
| Sodium Cocoylglucoside Tartrate | — | — | 3.0 | — | — | 2.0 | — | — |
| Coco Glucosides | — | — | — | 1.0 | 1.0 | 1.0 | 3.0 | 3.0 |
| Benzophenone-3 | 7.0 | — | — | — | — | — | 4.0 | — |
| 4-Methylbenzylidene Camphor | — | 7.0 | — | — | — | — | — | — |
| Isoamyl-p-Methoxycinnamate | — | — | 7.0 | — | — | — | — | — |
| Octyl Methoxycinnamate | — | — | — | 7.0 | — | — | — | — |
| Octyl Triazone | — | — | — | — | 7.0 | — | — | — |
| Titanium Dioxide | — | — | — | — | — | 9.0 | — | 9.0 |
| Water |  |  |  | to 100 |  |  |  |  |
| Stability |  |  |  |  |  |  |  |  |
| after 1 week, 20° C. | ++ | ++ | ++ | ++ | ++ | ++ | ++ | ++ |
| after 2 weeks, 20° C. | ++ | ++ | ++ | ++ | ++ | ++ | ++ | ++ |
| after 4 weeks, 20° C. | ++ | ++ | ++ | ++ | ++ | ++ | + | + |
| after 1 week, 40° C. | ++ | ++ | ++ | ++ | ++ | ++ | ++ | + |
| after 2 weeks, 40° C. | ++ | ++ | ++ | ++ | ++ | ++ | + | − |
| after 4 weeks, 40° C. | + | + | + | ++ | ++ | ++ | − | − |

What is claimed is:
1. A cosmetic preparation comprising:
(a) an ester corresponding to the general formula (I):

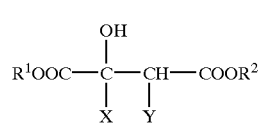
(I)

wherein X represents a hydrogen or a —$CH_2COOR^3$ substituent, Y represents a hydrogen or a hydroxyl substituent, $R^1$, $R^2$ and $R^3$ each independently represents a substituent selected from the group consisting of hydrogen, alkali metals, alkaline earth metals, ammonium, alkyl ammoniums, hydroxyalkyl ammoniums, glucammonium, and residues of alk(en)yl oligoglycosides corresponding to the general formula (II):

(II)

wherein $R^4$ represents an alk(en)yl group having from 4 to 22 carbon atoms, G represents a sugar unit containing 5 or 6 carbon atoms and p is a number of from 1 to 10; wherein at least one of $R^1$, $R^2$ and $R^3$ represents a residue of an alk(en)yl oligoglycoside corresponding to the general formula (II), and with the proviso that, where X represents a —$CH_2COOR^3$ group, Y is hydrogen; and (b) a UV protection factor.

2. The cosmetic preparation according to claim 1, further comprising an unesterified alk(en)yl oligoglycoside corresponding to the general formula (II).

3. The cosmetic preparation according to claim 2, wherein the unesterified alk(en)yl oligoglycoside is present in an amount of from 1 to 50% by weight, based on the ester and UV protection factor combined.

4. The cosmetic preparation according to claim 2, wherein the unesterified alk(en)yl oligoglycoside is present in an amount of from 5 to 25% by weight, based on the ester and UV protection factor combined.

5. The cosmetic preparation according to claim 1, wherein the ester is present in an amount of from 0.1 to 15% by weight.

6. The cosmetic preparation according to claim 1, wherein the UV protection factor is present in an amount of from 0.1 to 25% by weight.

7. The cosmetic preparation according to claim 1, wherein the ester is present in an amount of from 0.5 to 10% by weight.

8. The cosmetic preparation according to claim 1, wherein the UV protection factor is present in an amount of from 0.5 to 10% by weight.

9. The cosmetic preparation according to claim 1, wherein the ester is present in an amount of from 0.1 to 15% by weight; and wherein the UV protection factor is present in an amount of from 0.1 to 25% by weight.

10. The cosmetic preparation according to claim 1, wherein the ester is a product of a reaction between an alk(en)yl oligoglycoside corresponding to the general formula (II) and a hydroxycarboxylic acid selected from the group consisting of malic acid, tartaric acid, citric acid, and mixtures thereof.

11. The cosmetic preparation according to claim 10, wherein the ester is present in an amount of from 0.1 to 15% by weight.

12. The cosmetic preparation according to claim 10, wherein the UV protection factor is present in an amount of from 0.1 to 25% by weight.

13. The cosmetic preparation according to claim 10, wherein the ester is present in an amount of from 0.5 to 10% by weight.

14. The cosmetic preparation according to claim 10, wherein the UV protection factor is present in an amount of from 0.5 to 10% by weight.

15. The cosmetic preparation according to claim 10, wherein the ester is present in an amount of from 0.1 to 15% by weight; and wherein the UV protection factor is present in an amount of from 0.1 to 25% by weight.

16. A cosmetic preparation comprising:

(a) an ester which is a reaction product of an alk(en)yl oligoglycoside and a hydroxycarboxylic acid selected from the group consisting of malic acid, tartaric acid, citric acid, and mixtures thereof, the ester corresponding to the general formula (I):

wherein X represents a hydrogen or a —$CH_2COOR^3$ substituent, Y represents a hydrogen or a hydroxyl substituent, $R^1$, $R^2$ and $R^3$ each independently represents a substituent selected from the group consisting of hydrogen, alkali metals, alkaline earth metals, ammonium, alkyl ammoniums, hydroxyalkyl ammoniums, glucammonium, and residues of alk(en)yl oligoglycosides corresponding to the general formula (II):

wherein $R^4$ represents an alk(en)yl group having from 8 to 16 carbon atoms, G represents a sugar unit containing 6 carbon atoms and p is a number of from 1 to 3; wherein at least one of $R^1$, $R^2$ and $R^3$ represents a residue of an alk(en)yl oligoglycoside corresponding to the general formula (II), and with the proviso that, where X represents a —$CH_2COOR^3$ group, Y is hydrogen; and (b) a UV protection factor; and (c) an unesterified alk(en)yl oligoglycoside corresponding to the general formula (II), present in an amount of from 5 to 25% by weight, based on the ester and UV protection factor combined;

wherein the ester is present in an amount of from 0.1 to 15% by weight; and wherein the UV protection factor is present in an amount of from 0.1 to 25% by weight.

17. A method of preparing a cosmetic emulsion, said method comprising:

(a) providing a UV protection factor;
(b) providing an ester corresponding to the general formula (I):

wherein X represents a hydrogen or a —$CH_2COOR^3$ substituent, Y represents a hydrogen or a hydroxyl substituent, $R^1$, $R^2$ and $R^3$ each independently represents a substituent selected from the group consisting of hydrogen, alkali metals, alkaline earth metals, ammonium, alkyl ammoniums, hydroxyalkyl ammoniums, glucammonium, and residues of alk(en)yl oligoglycosides corresponding to the general formula (II):

wherein $R^4$ represents an alk(en)yl group having from 4 to 22 carbon atoms, G represents a sugar unit containing 5 or 6 carbon atoms and p is a number of from 1 to 10; wherein at least one of $R^1$, $R^2$ and $R^3$ represents a residue of an alk(en)yl oligoglycoside corresponding to the general formula (II), and with the proviso that, where X represents a —CH$_2$COOR$^3$ group, Y is hydrogen; and (c) mixing the UV protection factor and the ester together to form an emulsion.

18. The method according to claim 17, wherein the ester is a product of a reaction between an alk(en)yl oligoglycoside corresponding to the general formula (II) and a hydroxycarboxylic acid selected from the group consisting of malic acid, tartaric acid, citric acid, and mixtures thereof.

19. The method according to claim 17, wherein the ester is present in an amount of from 0.1 to 15% by weight.

20. The method according to claim 17, wherein the UV protection factor is present in an amount of from 0.1 to 25% by weight.

* * * * *